(12) United States Patent
Santella

(10) Patent No.: US 8,633,226 B2
(45) Date of Patent: *Jan. 21, 2014

(54) PIPERIDINYL DERIVATIVE AS A MODULATOR OF CHEMOKINE RECEPTOR ACTIVITY

(71) Applicant: Bristol-Myers Squibb Company, Princeton, NJ (US)

(72) Inventor: Joseph B. Santella, Springfield, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/628,180

(22) Filed: Sep. 27, 2012

(65) Prior Publication Data

US 2013/0023564 A1  Jan. 24, 2013

Related U.S. Application Data

(63) Continuation of application No. 12/490,477, filed on Jun. 24, 2009, now Pat. No. 8,299,098.

(60) Provisional application No. 61/075,394, filed on Jun. 25, 2008.

(51) Int. Cl.
*A61K 31/445* (2006.01)
*C07D 211/00* (2006.01)

(52) U.S. Cl.
USPC .......................... 514/327; 546/217

(58) Field of Classification Search
USPC .......................... 514/327; 546/217
See application file for complete search history.

(56) References Cited

U.S. PATENT DOCUMENTS

| | | | |
|---|---|---|---|
| 4,764,618 | A | 8/1988 | Kikumoto et al. |
| 5,492,920 | A | 2/1996 | Chen et al. |
| 5,847,148 | A | 12/1998 | Jacobsen et al. |
| 6,194,448 | B1 | 2/2001 | Biediger et al. |
| 6,344,449 | B1 | 2/2002 | Rudolf et al. |
| 6,391,865 | B1 | 5/2002 | Baroudy et al. |
| 6,489,354 | B1 | 12/2002 | Bao et al. |
| 6,638,950 | B2 | 10/2003 | Duncia et al. |
| 6,794,507 | B2 | 9/2004 | Cappi et al. |
| 6,846,836 | B2 | 1/2005 | Hamann et al. |
| 7,601,844 | B2 | 10/2009 | Carter et al. |
| 7,615,556 | B2 | 11/2009 | Carter et al. |
| 8,299,098 | B2* | 10/2012 | Santella ................ 514/327 |
| 2003/0162764 | A1 | 8/2003 | Castelhano et al. |
| 2003/0229067 | A1 | 12/2003 | Castelhano et al. |
| 2004/0006067 | A1 | 1/2004 | Fotsch et al. |
| 2005/0227968 | A1 | 10/2005 | Lustenberger et al. |
| 2005/0250814 | A1 | 11/2005 | Zhou et al. |
| 2006/0004018 | A1 | 1/2006 | Xue et al. |
| 2007/0123509 | A1 | 5/2007 | Cezanne et al. |
| 2007/0179148 | A1 | 8/2007 | Carter et al. |
| 2007/0208056 | A1 | 9/2007 | Carter et al. |
| 2009/0298833 | A1 | 12/2009 | Carter et al. |
| 2010/0204274 | A1 | 8/2010 | Gardner et al. |
| 2011/0245226 | A1 | 10/2011 | Carter et al. |

FOREIGN PATENT DOCUMENTS

| | | |
|---|---|---|
| DE | 4243858 | 6/1994 |
| EP | 0838460 | 4/1998 |
| JP | 2001/354657 | 12/2000 |
| WO | WO 92/15304 | 9/1992 |
| WO | WO 94/25437 | 11/1994 |
| WO | WO 95/34311 | 12/1995 |
| WO | WO 97/38665 | 10/1997 |
| WO | WO 98/17625 | 4/1998 |
| WO | WO 99/08697 | 2/1999 |
| WO | WO 99/08699 | 2/1999 |
| WO | WO 00/35874 | 6/2000 |
| WO | WO 00/74679 | 12/2000 |
| WO | WO 02/059117 | 8/2002 |
| WO | WO 02/070511 | 9/2002 |
| WO | WO 02/092682 | 11/2002 |
| WO | WO 03/007949 | 1/2003 |

(Continued)

OTHER PUBLICATIONS

Baraldi, P. et al., "Synthesis and biological activity of N-arylpiperazine-modified analogues of KN-62, a potent antagonist of the purinergic P2X$_7$ receptor", J. Med. Chem., vol. 46, pp. 1318-1320 (2003).

(Continued)

*Primary Examiner* — Shengjun Wang
(74) *Attorney, Agent, or Firm* — Hong Liu; Laurelee A. Duncan

(57) ABSTRACT

The present application describes the compound of formula (I):

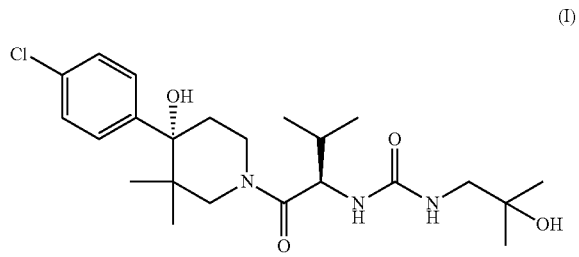

(I)

or stereoisomers or pharmaceutically acceptable salts thereof. In addition, methods of treating and preventing inflammatory diseases such as asthma and allergic diseases, as well as autoimmune pathologies such as rheumatoid arthritis and arthrosclerosis using the compound of the invention are disclosed.

8 Claims, No Drawings

(56) References Cited

FOREIGN PATENT DOCUMENTS

| | | |
|---|---|---|
| WO | WO 03/009847 | 2/2003 |
| WO | WO 03/022835 | 3/2003 |
| WO | WO 03/092688 | 11/2003 |
| WO | WO 03/105853 | 12/2003 |
| WO | WO 2004/037796 | 5/2004 |
| WO | WO 2004/043965 | 5/2004 |
| WO | WO 2004/076418 | 9/2004 |
| WO | WO 2004/113323 | 12/2004 |
| WO | WO 2005/003127 | 1/2005 |
| WO | WO 2005/054227 | 6/2005 |
| WO | WO 2005/056015 | 6/2005 |
| WO | WO 2005/084672 | 9/2005 |
| WO | WO 2005/118579 | 12/2005 |
| WO | WO 2006/004741 | 1/2006 |
| WO | WO 2006/013073 | 2/2006 |
| WO | WO 2007/092681 | 8/2007 |
| WO | WO 2009/015164 | 1/2009 |
| WO | WO 2009/015166 | 1/2009 |
| WO | WO2013/013114 | 1/2013 |

OTHER PUBLICATIONS

Carson, K. et al., "CCR1 Antagonists", Annual Reports in Medicinal Chemistry, vol. 39, pp. 149-158 (2004).

Lang, L. et al., (Database Beilstein, Beilstein Institute for Organic Chemistry, BRN#: 8854794), J. Labelled Compd. Radiopharm., vol. 44, pp. S21-S23 (2001).

Oshiro, Y. et al., "Novel cerebroprotective agents with central nervous system stimulating activity. 2. Synthesis and pharmacology of the 1-(acylamino)-7-hydroxyindan derivatives", J. Med. Chem., vol. 34, No. 7, pp. 2014-2023 (1991).

Pessoa-Mahana, H. et al., "Synthesis of 4-arylpiperazine derivatives of moclobemide: Potential antidepressants with a dual mode of action", Synthetic Communications, vol. 34, No. 14, pp. 2513-2521 (2004).

Richardson, T. et al., "Synthesis and structure-activity relationships of novel arylpiperazines as potent and selective agonists of the melanocortin subtype-4 receptor", J. Med. Chem., vol. 47, pp. 744-755 (2004).

Tiwari, M., (Database Beilstein, Beilstein Institute for Organic Chemistry, BRN#: 943608, 944316), J. Indian Chem. Soc., vol. 53, pp. 310-311 (1976).

F.Z. Dorwald "Side Reactions in Organic Synthesis: A Guide to Successful Synthesis Design" 2005, Wiley-VCH Verlag GMBH & Co. KGaA, Wienheim.

Office Action of U.S. Appl. No. 13/155,460, Modification Date, May 14, 2012.

* cited by examiner

PIPERIDINYL DERIVATIVE AS A MODULATOR OF CHEMOKINE RECEPTOR ACTIVITY

RELATED APPLICATION

This application claims the benefit of U.S. Provisional Application No. 61/075,394, filed on Jun. 25, 2008, incorporated herein by reference in its entirety.

FIELD OF THE INVENTION

This invention relates generally to a piperidinyl modulator of chemokine receptor activity, pharmaceutical compositions containing the same, and methods of using the same as an agent for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils. There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (−1 and −2) are chemotactic for, among other cell types, macrophages, T lymphocytes, eosinophils, dendritic cells, and basophils.

The chemokines bind to specific cell-surface receptors belonging to the family of G-protein-coupled seven-transmembrane-domain proteins which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] CCR-2A and CCR-2B (or "CKR-2A"/"CKR-2B" or "CC-CKR-2A"/"CC-CKR-2B") [MCP-1, MCP-2, MCP-3, MCP-4, MCP-5]; CCR-3 (or "CKR-3" or "CC-CKR-3") [eotaxin-1, eotaxin-2, RANTES, MCP-3, MCP-4]; CCR-4 (or "CKR-4" or "CC-CKR-4") [TARC, MDC]; CCR-5 (or "CKR-5" OR "CC-CKR-5") [MIP-1α, RANTES, MIP-1β]; CCR-6 (or "CKR-6" or "CC-CKR-6") [LARC]; CCR-7 (or "CKR-7" or "CC-CKR-7") [ELC]; CCR-8 (or "CKR-8" or "CC-CKR-8") [I-309]; CCR-10 (or "CKR-10" or "CC-CKR-10") [MCP-1, MCP-3]; and CCR-11 [MCP-1, MCP-2, and MCP-4].

In addition to the mammalian chemokine receptors, mammalian cytomegaloviruses, herpesviruses and poxviruses have been shown to express, in infected cells, proteins with the binding properties of chemokine receptors. Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and arthrosclerosis (reviewed in: Carter, P. H., *Current Opinion in Chemical Biology* 2002, 6, 510; Trivedi et al., *Ann. Reports Med. Chem.* 2000, 35, 191; Saunders et al., *Drug Disc. Today* 1999, 4, 80; Premack et al., *Nature Medicine* 1996, 2, 1174). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E., *J. Immun.* 2000, 164, 3392-3401).

Demonstration of the importance of the MIP-1α/CCR-1 interaction has been provided by experiments with genetically modified mice. MIP-1α −/− mice had normal numbers of leukocytes, but were unable to recruit monocytes into sites of viral inflammation after immune challenge. Recently, MIP-1α −/− mice were shown to be resistant to collagen antibody induced arthritis. Likewise, CCR-1 −/− mice were unable to recruit neutrophils when challenged with MIP-1α in vivo; moreover, the peripheral blood neutrophils of CCR-1 null mice did not migrate in response to MIP-1α, thereby demonstrating the specificity of the MIP-1α/CCR-1 interaction. The viability and generally normal health of the MW-1α −/− and CCR-1 −/− animals is noteworthy, in that disruption of the MIP-1α/CCR-1 interaction does not induce physiological crisis. Taken together, these data lead one to the conclusion that molecules that block the actions of MIP-1α would be useful in treating a number of inflammatory and autoimmune disorders. This hypothesis has now been validated in a number of different animal disease models, as described below.

It is known that MIP-1α is elevated in the synovial fluid and blood of patients with rheumatoid arthritis. Moreover, several studies have demonstrated the potential therapeutic value of antagonism of the MIP-1α/CCR1 interaction in treating rheumatoid arthritis.

It should also be noted that CCR-1 is also the receptor for the chemokines RANTES, MCP-3, HCC-1, Lkn-1/HCC-2, HCC-4, and MPIF-1 (Carter, P. H., *Curr. Opin Chem. Bio.* 2002, 6, 510-525). Since it is presumed that the new compound of formula (I) described herein antagonizes MIP-1α by binding to the CCR-1 receptor, it may be that this compound is also an effective antagonist of the actions of the aforementioned ligand that are mediated by CCR-1. Accordingly, when reference is made herein to "antagonism of MIP-1α," it is to be assumed that this is equivalent to "antagonism of chemokine stimulation of CCR-1."

Recently, a number of groups have described the development of small molecule antagonists of MIP-1α (reviewed in: Carson, K. G. et al., *Ann. Reports Med. Chem.* 2004, 39, 149-158).

SUMMARY OF THE INVENTION

Accordingly, the present invention provides an antagonist or partial agonist/antagonist of MIP-1α or CCR-1 receptor activity, or pharmaceutically acceptable salts thereof.

The present invention provides pharmaceutical compositions comprising a pharmaceutically acceptable carrier and a therapeutically effective amount of the compound of the present invention or a pharmaceutically acceptable salt form thereof.

The present invention provides a method for treating rheumatoid arthritis and transplant rejection, comprising administering to a host in need of such treatment a therapeutically effective amount of the compound of the present invention or a pharmaceutically acceptable salt form thereof.

The present invention provides a method for treating inflammatory diseases, comprising administering to a host in need of such treatment a therapeutically effective amount of the compounds of the present invention or a pharmaceutically acceptable salt form thereof.

The present invention provides a piperidinyl derivative for use in therapy.

The present invention provides the use of a piperidinyl derivative for the manufacture of a medicament for the treatment of inflammatory diseases.

DETAILED DESCRIPTION OF THE INVENTION

In one embodiment, the present invention provides a compound of formula (I):

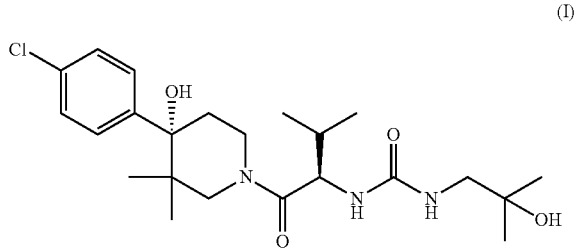 [SMILES: CC(C)[C@@H](NC(=O)NCC(C)(C)O)C(=O)N1CC[C@](O)(c2ccc(Cl)cc2)C(C)(C)C1]

(I)

or stereoisomers or pharmaceutically acceptable salts thereof.

The present invention provides a piperidinyl compound that has an unexpectedly advantageous profile as compared to known inhibitors of CCR-1 activity, for example, the piperidinyl derivatives described in application US2007/0208056 A1, published Sep. 6, 2007, and assigned to applicant. More preferably, the compound exhibits a superior safety profile with minimal drug-drug interaction and other properties that make it an attractive candidate for clinical development. Accordingly, it is these unexpected properties alone and/or in combination that make the compound of formula (I) desirable for use as a pharmaceutical agent.

In another embodiment, the present invention is directed to a pharmaceutical composition, comprising a pharmaceutically acceptable carrier and a therapeutically effective amount of a compound of formula (I).

In another embodiment, the present invention is directed to a method for modulation of chemokine or chemokine receptor activity comprising administering to a patient in need thereof a therapeutically effective amount of a compound of formula (I).

In another embodiment, the present invention is directed to a method for modulation of CCR-1 receptor activity comprising administering to a patient in need thereof a therapeutically effective amount of a compound of formula (I).

In another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a compound of formula (I).

In another embodiment, the present invention is directed to a method for treating disorders, comprising administering to a patient in need thereof a therapeutically effective amount of a compound of formula (I), wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, neuropathic pain, inflammatory bowel disease, alveolitis, ulcerative colitis, systemic lupus erythematosus, nephrotoxic serum nephritis, glomerulonephritis, asthma, multiple sclerosis, arthrosclerosis, rheumatoid arthritis, restenosis, organ transplantation, psoriatic arthritis, multiple myeloma, allergies, for example, skin and mast cell degranulation in eye conjunctiva, hepatocellular carcinoma, colorectal cancer, osteoporosis, renal fibrosis, and other cancers, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, comprising administering to a patient in need thereof a therapeutically effective amount of a compound of formula (I).

In another embodiment, the present invention is directed to a method for treating inflammatory bowel disease, comprising administering to a patient in need thereof a therapeutically effective amount of a compound of formula (I).

In another embodiment, the present invention is directed to a method for treating Crohn's disease, comprising administering to a patient in need thereof a therapeutically effective amount of a compound of formula (I).

In another embodiment, the present invention is directed to a method for treating psoriasis, comprising administering to a patient in need thereof a therapeutically effective amount of a compound of formula (I).

In another embodiment, the present invention is directed to a method for treating systemic lupus erythematosus, comprising administering to a patient in need thereof a therapeutically effective amount of a compound of formula (I).

In another embodiment, the present invention is directed to a method for treating multiple sclerosis, comprising administering to a patient in need thereof a therapeutically effective amount of a compound of formula (I).

In another embodiment, the present invention is directed to a method for treating rheumatoid arthritis, comprising administering to a patient in need thereof a therapeutically effective amount of a compound of formula (I).

In another embodiment, the present invention is directed to a method for treating psoriatic arthritis, comprising administering to a patient in need thereof a therapeutically effective amount of a compound of formula (I).

In another embodiment, the present invention is directed to a method for treating multiple myeloma, comprising administering to a patient in need thereof a therapeutically effective amount of a compound of formula (I).

In another embodiment, the present invention is directed to a method for treating allergies, for example, skin and mast cell degranulation in eye conjunctiva, comprising administering to a patient in need thereof a therapeutically effective amount of a compound of formula (I).

In another embodiment, the present invention is directed to a method for treating hepatocellular carcinoma, comprising administering to a patient in need thereof a therapeutically effective amount of a compound of formula (I).

In another embodiment, the present invention is directed to a method for treating osteoporosis, comprising administering to a patient in need thereof a therapeutically effective amount of a compound of formula (I).

In another embodiment, the present invention is directed to a method for treating renal fibrosis, comprising administering to a patient in need thereof a therapeutically effective amount of a compound of formula (I).

In another embodiment, the present invention is directed to a method for treating inflammatory diseases, for example, inflammatory diseases which are at least partially mediated by CCR-1, comprising administering to a patient in need thereof a therapeutically effective amount of a compound of formula (I).

In another embodiment, the present invention is directed to a method for modulation of CCR1 activity comprising administering to a patient in need thereof a therapeutically effective amount of a compound of formula (I).

In another embodiment, the present invention is directed the use of a compound of formula (I) in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, neuropathic pain, inflammatory bowel disease, alveolitis, ulcerative colitis, systemic lupus erythematosus, nephrotoxic serum nephritis, glomerulonephritis, asthma, multiple sclerosis, arthrosclerosis, rheumatoid arthritis, restenosis, organ transplantation, psoriatic arthritis, multiple myeloma, allergies, for example, skin and mast cell degranulation in eye conjunctiva, hepatocellular carcinoma, colorectal cancer, osteoporosis, renal fibrosis and other cancers, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a compound of formula (I) for use in therapy.

In another embodiment, the present invention is directed to a pharmaceutical composition comprising a compound of formula (I) and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of formula (I) and one or more active ingredients.

In another embodiment, the present invention is directed to a method for modulation of CCR-1 receptor activity comprising administering to a patient in need thereof a therapeutically effective amount of a pharmaceutical composition comprised of a compound of formula (I) and one or more active ingredients.

In yet another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a pharmaceutical composition comprised of a compound of formula (I) and one or more active ingredients.

In another embodiment, the present invention is directed to a method for treating a disorder, comprising administering to a patient in need thereof a therapeutically effective amount of a pharmaceutical composition comprised of a compound of formula (I) and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, neuropathic pain, inflammatory bowel disease, alveolitis, ulcerative colitis, systemic lupus erythematosus, nephrotoxic serum nephritis, glomerulonephritis, asthma, multiple sclerosis, arthrosclerosis, rheumatoid arthritis, restenosis, organ transplantation, psoriatic arthritis, multiple myeloma, allergies, for example, skin and mast cell degranulation in eye conjunctiva, hepatocellular carcinoma, colorectal cancer, osteoporosis, renal fibrosis and other cancers, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-1, comprising administering to a patient in need thereof a therapeutically effective amount of a pharmaceutical composition comprised of a compound of formula (I) and one or more active ingredients.

In another embodiment, the present invention is directed to a method for modulation of CCR-1 activity comprising administering to a patient in need thereof a therapeutically effective amount of a pharmaceutical composition comprised of a compound of formula (I) and one or more active ingredients.

In another embodiment, the present invention is directed to the use of a pharmaceutical composition comprised of a compound of formula (I) and one or more active ingredients in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, neuropathic pain, inflammatory bowel disease, alveolitis, ulcerative colitis, systemic lupus erythematosus, nephrotoxic serum nephritis, glomerulonephritis, asthma, multiple sclerosis, arthrosclerosis, rheumatoid arthritis, restenosis, organ transplantation, psoriatic arthritis, multiple myeloma, allergies, for example, skin and mast cell degranulation in eye conjunctiva, hepatocellular carcinoma, colorectal cancer, osteoporosis, renal fibrosis and other cancers, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of a compound of formula (I) and one or more active ingredients in therapy.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent as known to one of ordinary skill in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compound of formula I was prepared as shown in the following Example, reaction scheme and descriptions thereof, as well as relevant literature procedures that may be used by one skilled in the art. Exemplary reagents and procedures for these reactions appear hereinafter.

EXAMPLE

Step 1: tert-Butyl 3,3-dimethyl-4-oxopiperidine-1-carboxylate

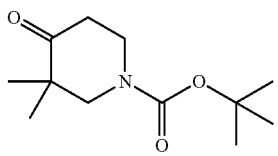 [SMILES: CC(C)(C)OC(=O)N1CCC(=O)C(C)(C)C1]

A solution of tert-butyl 4-oxopiperidine-1-carboxylate (52.47 g, 263 mmol) in THF (1000 mL) was cooled to 0° C. and treated with sodium hydride (60% suspension in mineral oil) (22.12 g, 553 mmol) in 4 equal portions at 5 minute intervals. The resulting suspension was stirred at 0° C. for 45 minutes ("min."), and then treated with the dropwise addition of iodomethane (41.2 ml, 658 mmol). The mixture was stirred for 1 hour ("h" or "hr"), and then allowed to come to room temperature ("rt"). Ninety minutes after the ice bath was removed, a rapid exotherm (20-40° C. in 3 minutes) and vigorous gas evolution was observed. The ice bath was replaced, and the mixture was allowed to stir overnight as it slowly warmed to room temperature. The reaction was quenched with saturated ammonium chloride (200 mL) then treated with enough water to dissolve the salts which had precipitated. The layers were separated and the organic phase was concentrated in vacuo. The aqueous phase was extracted with ethyl acetate, and this extract was combined with the residue from the first organic phase. The resulting solution was diluted with 500 ml ethyl acetate, and the mixture was washed 2 times ("x") with water, once with brine, dried over sodium sulfate and then concentrated in vacuo to yield a viscous oil which solidified upon standing. The solidified cake was dissolved in 100 mL, of boiling hexanes, and the resulting solution was allowed to cool to room temperature where it stood overnight. After this time, crystals that had precipitated were collected by filtration, rinsed with a small amount of ice-cold hexanes, and dried to yield the title compound as a powder (19.5 g, 86 mmol, 32.6% yield). MS (ES+)=172, 154.

Step 2: (±)-tert-Butyl 4-(4-chlorophenyl)-4-hydroxy-3,3-dimethylpiperidine-1-carboxylate

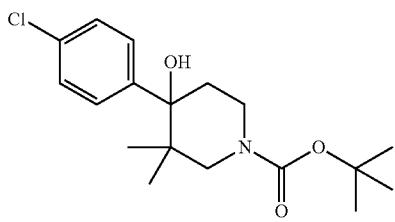 [SMILES: CC(C)(C)OC(=O)N1CCC(O)(c2ccc(Cl)cc2)C(C)(C)C1]

A solution of 4-bromochlorobenzene (136.6 g, 0.71 mol) in anhydrous THF (1000 mL) was cooled to −78° C., and then treated dropwise with a 1.6 M solution of n-butyllithium in hexanes (466 mL, 0.75 mol) at a rate which maintained the internal temperature below −60° C. The resulting mixture was stirred at −78° C. for 1.5 hours, during which a precipitate was observed. The resulting suspension was treated dropwise with a solution of tert-butyl 3,3-dimethyl-4-oxopiperidine-1-carboxylate (73.7 g, 0.32 mol) in anhydrous THF (400 mL) at a rate which maintained the internal temperature below −60° C. The mixture was stirred at −78° C. for 2 hours, during which a clear solution was observed. The reaction mixture was quenched with saturated ammonium chloride (300 mL) and the resulting mixture was allowed to come to room temperature. The aqueous and organic layers were separated, and the organic phase was concentrated in vacuo to yield a residue. The aqueous phase was extracted 2× with ethyl acetate (300 mL). The combined extracts were added to the residue from the original organic phase, and the resulting mixture was diluted to 1200 mL with ethyl acetate. The resulting solution was washed 2× with water (300 mL), once with brine, dried over sodium sulfate, and concentrated in vacuo to yield a residue. The residue was digested with boiling hexanes (300 mL), and the resulting suspension was cooled to room temperature. Once at the prescribed temperature, white solids were collected by filtration, and washed 2× with hexanes and then air dried to yield the title compound as a powder (93.7 g, 85% yield).

Step 3: (±)-4-(4-Chlorophenyl)-3,3-dimethylpiperidin-4-ol

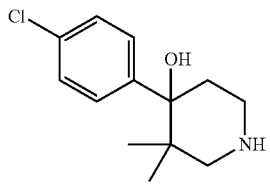 [SMILES: CC1(C)CNCCC1(O)c1ccc(Cl)cc1]

A solution of (±)-tert-butyl 4-(4-chlorophenyl)-4-hydroxy-3,3-dimethylpiperidine-1-carboxylate (93.7 g, 0.276 mol) in dioxane (100 mL) was treated with 4 M HCl solution in dioxane (275 mL, 1.1 mol). The resulting mixture was stirred at room temperature for four hours. After this time, the mixture was concentrated in vacuo, and then concentrated 3× from methylene chloride (200 mL) to remove residual HCl. The resulting residue was stirred in 1 M NaOH (500 mL), and the resulting suspension was extracted 4× with 500 mL of ethyl acetate. The combined organic phases were washed with brine, dried over sodium sulfate, and concentrated in vacuo to yield the title compound (66.8 g, quantitative yield) as a solid.

Step 4: (S)-4-(4-Chlorophenyl)-3,3-dimethylpiperidin-4-ol

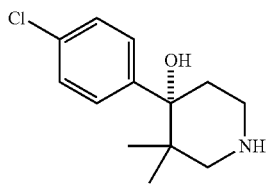

A suspension of (±)-4-(4-chlorophenyl)-3,3-dimethylpiperidin-4-ol (175 g) and L-tartaric acid (0.9 equiv) in MEK (3.22 L) was heated to reflux. Once at the prescribed temperature, water (100 mL) was added to achieve a solution. The resulting solution was heated at reflux for 1 h and then allowed to cool to room temperature where it stirred for 48 h. After this time, the resulting slurry was filtered and the collected solids were dried under vacuum to give 123.4 grams of the tartaric acid salt. This material was combined with another run of the same scale and the combined solids were suspended in MEK (2.55 L) and water (0.25 L). The resulting solution was heated to reflux and additional water (0.2 L) was added to solubilize the mixture. The solution was heated at reflux for 2 h and then allowed to cool to room temperature, where it stirred over the weekend. At the conclusion of this period, the resulting solids were collected by filtration and dried to give 219 g of the salt. The salt was divided into two equal portions. Each portion was suspended in water (2 L) and then 50% NaOH was added to precipitate the free base of the piperidine. After filtering and drying, 126.3 g of the title compound was isolated (~72% yield, >99% ee).

Step 5: tert-Butyl(R)-1-(S)-4-(4-chlorophenyl)-4-hydroxy-3,3-dimethylpiperidin-1-yl)-3-methyl-1-oxobutan-2-ylcarbamate

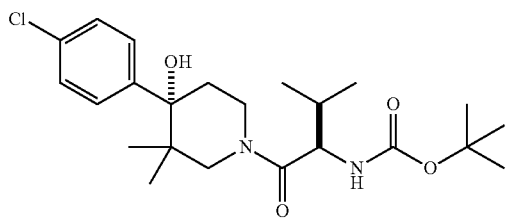 [SMILES: CC(C)[C@@H](NC(=O)OC(C)(C)C)C(=O)N1CC[C@](O)(c2ccc(Cl)cc2)C(C)(C)C1]

To a 3L three neck roundbottom ("RB") flask was added (R)-2-(tert-butoxycarbonylamino)-3-methylbutanoic (39.8 g, 183 mmol), CH₂Cl₂ (1.6 L), (S)-4-(4-chlorophenyl)-3,3-dimethylpiperidin-4-ol (40.0 g, 167 mmol), EDC (70.4 g, 367 mmol), and HOBt (56.2 g, 416 mmol). Upon completion of addition, the reaction mixture was stirred for 30 min. at rt. After this time, triethyl amine (TEA, 93 mL, 668 mmol) was added. The resulting mixture was stirred at room temperature for 20 h. At the conclusion of this period, the reaction mixture was washed with Na₂CO₃ (3×300 mL, note: the first Na₂CO₃ wash, was vacuum filtered and the resulting filtrate was back extracted with CH₂Cl₂), 1N HCl (3×300 mL), water (400 mL) and brine (300 mL). The resulting solution was dried over Na₂SO₄ and concentrated to a semi-solid (106 g, theoretical yield was 73.2g). The semi-solid was reacted in the next step without further purification.

Step 6: (R)-2-Amino-1-((S)-4-(4-chlorophenyl)-4-hydroxy-3,3-dimethylpiperidin-1-yl)-3-methylbutan-1-one, HCl

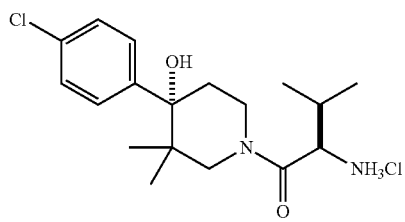

To a 1000 mL RB flask was added tert-butyl(R)-1-((S)-4-(4-chlorophenyl)-4-hydroxy-3,3-dimethylpiperidin-1-yl)-3-methyl-1-oxobutan-2-ylcarbamate (65 g, 148 mmol) and hydrogen chloride (4 M HCl in dioxane, 720 mL, 2880 mmol). Upon completion of addition, the reaction mixture was stirred at rt for 2.5 h. After this time, the reaction mixture was concentrated to yield a gel. The gel was co-evaporated with methanol (8×100 mL) and then CH₂Cl₂ (7×100mL) to yield a solid (initially weighing 57 g, HCl salt).

Step 7: Phenyl(R)-1-((S)-4-(4-chlorophenyl)-4-hydroxy-3,3-dimethylpiperidin-1-yl)-3-methyl-1-oxobutan-2-ylcarbamate

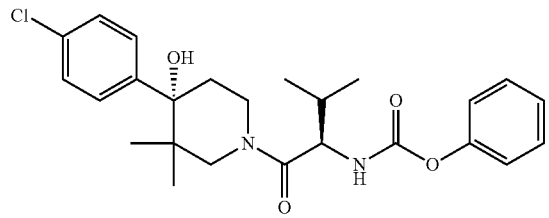 [SMILES: CC(C)[C@@H](NC(=O)Oc1ccccc1)C(=O)N1CC[C@](O)(c2ccc(Cl)cc2)C(C)(C)C1]

The carbamate synthesis was carried out in two separate flasks. The amounts disclosed herein are the totals used to carryout the experiments in the two flasks. (R)-2-amino-1-((S)-4-(4-chlorophenyl)-4-hydroxy-3,3-dimethylpiperidin-1-yl)-3-methylbutan-1-one, HCl (20 g, 53.3 mmol) and DIPEA (18.61 mL, 107 mmol) were mixed in CH₂Cl₂ (15 mL) at rt with stirring, and then phenyl carbonochloridate (6.71 mL, 53.3 mmol) in 10 ml of methylene chloride was added drop wise via an addition funnel. Upon completion of addition, the reaction mixture was stirred for one hour. After this time, an additional 0.2 equiv. of DIPEA followed by a solution of phenyl chloroformate in methylene chloride was added. The organic and aqueous layers were separated. The organic layer was washed with 1N HCl, sat aq. NaHCO₃, and brine; dried and then stripped to give an oil. To the oil, with stirring at rt, was added 25 ml of MeCN. Upon completion of addition, solids formed after stirring for 10 min. Ether (50 mL) was added and the resulting mixture was stirred for 5 minutes. After this time, additional ether (25 mL) was added and stirring was continued for 15 minutes. At the conclusion of this period, the resulting solids were collected by filtration and then rinsed with ether to give 13 grams of the crude solid which was used without further purification. The filtrate was concentrated to yield a residue. The residue was purified over silica gel (9:1 to 3:1 to 1:1 hexanes/EtOAc to 100% EtOAc) to give an additional 6.72 g of product 6.72 g (total mass yield 19.7 g, 81% yield).

Step 8: Compound of Formula (I)

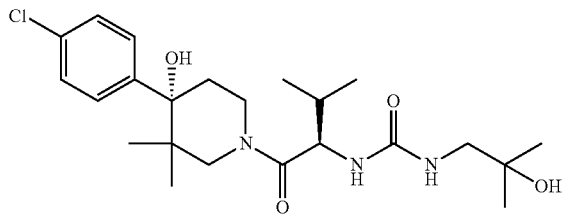

Under a nitrogen atmosphere, phenyl(R)-1-(S)-4-(4-chlorophenyl)-4-hydroxy-3,3-dimethylpiperidin-1-yl)-3-methyl-1-oxobutan-2-ylcarbamate (16.0 g, 34.9 mmol), 1-amino-2-methylpropan-2-ol (3.42 g, 38.3 mmol) and DIPEA (6.70 mL, 38.3 mmol) were mixed with stirring in MeCN (30 mL) at rt. The resulting suspension was heated to reflux, during which time the suspension became a colorless solution. After stirring at reflux for about 20 minutes, solids precipitated. After stirring at reflux for 1.5 h, 20 ml of acetonitrile and another 0.1 equiv. of 1-amino-2-methylpropan-2-ol and DIPEA were added. The reaction mixture was stirred for an additional 1.5 h. After this time, the reaction mixtured was removed from heating and allowed to cool to rt. While cooling to rt, water was added to precipitate the product (~240 mL) and the resulting free flowing suspension was stirred overnight. At the conclusion of this period, the resulting solids were collected by filtration, rinsed 2 times with water and then dried under high vacuum for 6 hours to give 15.4 grams of solids. These solids (and an additional ~1 gram of pilot batch) were slurried in 50 mL of acetone at rt with stirring, and then 3 times the volume of water (150 mL) was added. The free-flowing suspension was stirred overnight. After this time, the resulting solids were collected by filtration, rinsed twice with water and then dried for 48 h to give 15.2 grams of the Compound of Formula I as a solid. $^1$H NMR (500 MHz, methanol-$d_4$, rotameric) δppm 7.47 (dd, J=15.4, 8.8 Hz, 4 H), 7.31 (dd, J=8.5, 5.2 Hz, 4 H), 4.71 (dd, J=12.1, 6.1 Hz, 2 H), 4.54 (ddd, J12.9, 2.5, 2.2 Hz, 1 H), 3.98-4.08 (m, 2 H), 3.58-3.68 (m, 2 H), 3.48 (dd, J=12.9, 1.4 Hz, 1 H), 3.13-3.21 (m, 2 H), 3.06-3.14 (m, 4 H), 2.70 (td, J=13.6, 4.7 Hz, 1 H), 2.61 (td, J=13.5, 5.0 Hz, 1 H), 2.09 (dq, J=13.2, 6.6 Hz, 1 H), 1.95 (dq, J=13.3, 6.7 Hz, 1 H), 1.60 (ddd, J=13.9, 2.5, 2.3 Hz, 1 H), 1.51 (ddd, J=14.2, 2.6, 2.5 Hz, 1 H), 1.16 (s, 6 H), 1.14 (d, J=1.7 Hz, 6 H), 1.05 (d, J=7.2 Hz, 3 H), 0.98 (d, J=7.2 Hz, 3 H), 0.94 (d, J=6.6 Hz, 3 H), 0.91 (d, J=6.6 Hz, 3 H), 0.82 (s, 3 H), 0.81 (s, 3 H), 0.79 (s, 3 H), 0.75 (s, 3 H). $^{13}$C NMR (126 MHz, methanol-$d_4$) δppm 173.6, 173.3, 161.1, 160.8, 144.8, 144.6, 133.82(2 C, s), 130.2 (4 C, s), 128.3 (4 C, s), 76.0, 76.0, 71.7, 71.7, 55.9, 55.2, 55.1, 51.8 (2 C, s), 51.1, 43.0, 40.4, 39.9, 39.3, 34.8, 33.7, 33.1, 32.4, 27.2 (2 C, s), 27.1 (2 C, s), 23.1, 22.8, 21.4, 21.1, 20.3, 19.8, 17.9, 17.7, m/z: 454.2 [M+]$^+$.

UTILITY

In general, the compound of formula (I) has been shown to be a modulator of chemokine receptor activity. By displaying activity as a modulator of chemokine receptor activity, the compound of formula (I) is expected to be useful in the treatment of human diseases associated with chemokines and their cognate receptors.

Comparative Pharmacological Characteristics

Assays and data comparing the pharmacological characteristics of Example 1 and compounds found in US2007/0208056A1 (corresponding to WO 2007/092681) are presented below.

The compound of the present invention (Compound 1) has been compared to other compounds that have been found to be useful inhibitors of CCR-1 activity, and found to be especially advantageous. For example, the surprising advantage over the compounds is shown below in Tables 1 and 2.

Human CCR1 THP-1 Binding Assay

For radioligand competition studies, a final concentration of $1 \times 10^5$ THP-1 monocytic leukemia cells are combined with 100 µg of LS WGA PS beads (Amersham, Cat.#: RPNQ 0260) in 40 µL of assay buffer (RPMI 1640 without phenol red, 50 mM HEPES, 5 mM MgCl$_2$, 1 mM CaCl$_2$, 0.1% BSA). The THP-1 cell/bead mixture was added to each well of a 384-well assay plate (PerkinElmer, Cat. #:6007899) containing test compound in 3-fold serial dilution, with final concentrations ranging from 8 µM to 0.14 nM. A final concentration of 0.1 nM [$^{125}$I]-MIP-1α (PerkinElmer, Cat. #NEX298) in 20 µL assay buffer was added to the reaction. Unlabeled MIP-1α was added in excess to some wells to determine non-specific binding. Sealed assay plates were incubated at room temperature for 12 h then analyzed by LEADseeker™.

The competition data of the test compound over a range of concentrations is plotted as percentage inhibition of radioligand specifically bound in the absence of test compound (percent of total signal). After correcting for non-specific binding, IC$_{50}$ values are determined. The IC$_{50}$ value is defined as the concentration of test compound needed to reduce [$^{125}$I]-MIP-1α specific binding by 50% and is calculated using the four parameter logistic equation to fit the normalized data. The K$_i$ values are determined by application of the Cheng-Prusoff equation to the IC$_{50}$ values, where K$_i$=IC$_{50}$/(1+ligand concentration/K$_d$). The Kd of [$^{125}$I]-MIP-1α in THP-1 cells is 0.1 nM. Each experiment was run in duplicate.

hERG Patch Clamp Assay

Whole-cell patch-clamp was used to directly measure hERG tail currents in HEK-293 cells stably expressing the cloned hERG potassium channel α subunit. Effects of compounds were calculated by measuring inhibition of peak tail current. Experiments were carried out using an aqueous buffer with pH 7.4 at room temperature. There was no protein in the assay buffer. The test concentrations reported are nominal free drug levels.

Sodium and L-Type Calcium Channel Assays

Whole-cell patch-clamp was used to directly measure inward sodium currents in HEK-293 cells expressing the human cardiac sodium channel, SCN5A. After reach steady-state effect in the presence of drug, rate-dependence was assessed by stimulation at frequencies of 1 Hz and 4 Hz. Experiments were carried out using an aqueous buffer at pH 7.4 and at room temperature. There is no protein in the buffer and drug concentrations reported are nominal free drug levels. Test article was evaluated up to 10 μM (protein-free buffer). Rate-dependence of inhibition was assessed by stimulation at frequencies of 1 Hz and 4 Hz.

In addition to the potential for interaction with the L-type calcium channel, whole-cell patch-clamp was used to directly measure inward calcium currents in HEK-293 cells stably expressing the cloned human cardiac L-type Ca channel (α1C) and its β subunit. Effects of compounds were calculated by measuring inhibition of peak current. Experiments were carried out using an aqueous buffer at pH 7.4 and at room temperature. There is no protein in the buffer and drug concentrations reported are nominal free drug levels.

Electrocardiography in Anesthetized Rabbits

A dose-response study of test compound was conducted in anesthetized rabbits to assess the cardiac electrophysiologic profile established in the cellular ion channel assays.

Experiments were performed in propofol-fentanyl anesthetized closed-chest male rabbits. A body surface electrocardiogram (ECG) and an intra-cardiac His-bundle electrogram were continuously monitored and recorded during the studies, using a PoNeMah system and a Prucka electrophysiological recording system, respectively. Test compound was prepared on the day of study in a vehicle of PEG400:ethanol: water (1:1:1) at a dosing concentration of 30 mg/mL. Test compound (n=3) or vehicle (n=3) was given intravenously over 5 minutes via an infusion pump at incremental doses of 3, 10 and 30 mg/kg. The interval between doses was 10 minutes, allowing for a 5-minute test agent infusion and a 5-minute rest period. Blood was sampled at baseline (pre-drug infusion) and immediately at the end of each infusion. For the 30 mg/kg dose, additional blood samples were taken at 10, 20 and 30 minutes after the end of infusion.

PR interval, QRS duration and QT interval were averaged from a 1 minute ECG recording period at time of blood sampling. QT interval was corrected for heart rate effects using both Fridericia (QTcf) and Van der Water (QTcv) formulae. AH and HV intervals, representing A-V node conduction and His-Purkinje conduction, respectively, were assessed by manual measurements from the His-bundle electrogram. Data were expressed as percent change from pre-drug baseline (mean±SEM) for PR, QRS, AH and HV intervals as well as delta change from the pre-drug infusion baseline (mean±SEM) for QTc intervals. Changes of ≥10% in PR, QRS, and AH intervals, and 20% in HV interval, as well as >10 ms in QTc interval are considered significant based on experience with the model.

As shown below in Table 1, the in vivo data demonstrates the superior safety profile of Compound I. In particular, while showing a lower in vitro Ki as compared to the other compounds, Compound I also had a No Observed Effect Level (NOEL) in the rabbit of 10 mg/kg. While the compound of Example 491 had a similar NOEL, it had a higher absolute QT prolongation as well as a lower free fraction of circulating drug relative to Compound I.

TABLE 1

| In Vitro and In Vivo Cardiovascular Safety Profile | | | |
|---|---|---|---|
| | Compound I | EX# 491* | EX# 572* |
| In vitro EP Effect | | | |
| CCR1 Ki (nM) | 0.7 | 2.1 | 1.5 |
| hERG, % inh @ 30 μM | 29% | 27% | 32% |

TABLE 1-continued

| In Vitro and In Vivo Cardiovascular Safety Profile | | | |
|---|---|---|---|
| | Compound I | EX# 491* | EX# 572* |
| Na, % inh | 12% @ 10 μM | 13% @ 10 μM | 25% @ 10 μM |
| Ca, % inh | 29% @ 30 μM | 22% @ 10 μM | 19% @ 30 μM |
| Protein binding Human | 81% (rabbit 87%) | 95% (rabbit 94%) | 84% (rabbit 87%) |
| In Vivo EP Effect | | | |
| QTcf, delta QT effect | 12 ms | 17 ms | 22 ms |
| Dose | 30 mg/kg | 30 mg/kg | 10 mg/kg |
| Cmax: Total drug/Free drug | 202/26 μM | 138.5/5.5 μM | 48.6/6.3 μM |
| NOEL dose, | 10 mg/kg | 10 mg/kg | Not identified |
| Cmax: Total drug/Free drug | 65.2/8.5 μM | 77/3.1 μM | <10 mg/kg <48.6/6.3 μM |

(*)- Examples from US2007/0208056 as shown below:

Ex. 491

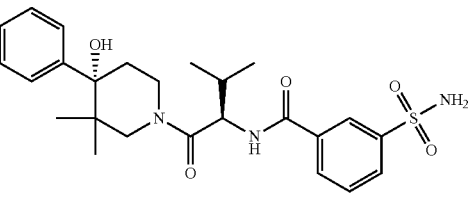

Ex. 572

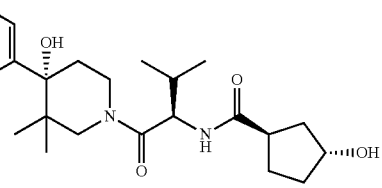

PXR Transactivation Assay

The cell culture medium used is DMEM. Lipofectamine 2000, PBS, heat-inactivated fetal bovine serum (FBS), trypsin-EDTA (0.25%), and penicillin-streptomycin were purchased from GIBCO/Invitrogen (Carlsbad, Calif.). Charcoal/dextran treated fetal bovine serum (FBS) was purchased from Hyclone (Logan, Utah). HepG2 cells were obtained from ATCC (Manassas, Va.). Human PXR-pcDNA3 and luciferase reporter containing CYP3A4 promoter, CYP3A-Luc, were generated at Bristol-Myers Squibb. White tissue culture (TC)-surface 384-well plates were purchased from Perkin Elmer (Boston, Mass.). Luciferase substrate (Steady-Glo) was purchased from Promega (Madison, Wis.). Control compounds rifampicin, mifepristone, and sulfinpyrazone were purchased from Sigma (St. Louis, Mo.).

Culture of HepG2 cells is performed in T175 flasks using DMEM containing 10% FBS. The transfection mixture contains 1 μg/mL of PXR-pcDNA3 plasmid DNA, 20 μg/ml of Cyp3A-Lue plasmid DNA, 90 μL/mL of Lipofectamine 2000, and serum-free medium. After incubating at room temperature for 20 minutes, the transfection mixture (1 ml per flask) is applied to the cells in fresh medium (20 mL per flask), and flasks incubated at 37° C. (5% $CO_2$) overnight.

Cells in each flask are washed with PBS and 2 mL of Trypsin-EDTA (0.25%) is added and incubated for five minutes at 37° C., 5% $CO_2$. The flasks are then tapped vigorously to break up cell aggregates. After the addition of 8 mL of DMEM containing 5% charcoal/dextran-treated FBS, the entire mixture is transferred to conical tubes. Cells are then centrifuged at 1000 rpm for 5 minutes. Cell pellets are resuspended to a final count of ~7×10$^6$ cells/ml, in freezing media (DMEM containing 20% serum and 10% DMSO). The cell suspension is aliquoted into 15-mL polypropylene tubes, 5 mL per tube. Cells are slowly frozen by placing in a Styrofoam-insulated container at −80° C. overnight. Vials are transferred to an Ultracold (−140° C.) freezer after 24 hours for long-term storage.

Vials of cryopreserved cells are thawed rapidly in a warm water bath for five minutes. Cells are pooled and diluted to 50 mL in a 50-mL conical vial. The thawed cells are centrifuged at 1500 rpm for 5 minutes to collect the cells and the supernatant discarded. Cells are then resuspended in fresh Media II (DMEM containing 5% charcoal/dextran-treated FBS, 1% Penicillin/Streptomycin, 100 μM Non-essential Amino Acids, 1 mM Sodium Pyruvate, and 2 mM L-Glutamine), counted using the Guava Cell Counter, and diluted to 1.6×10$^5$ cells/ml in the same media.

Fifty microliters of cell mixture is added to wells in columns 1-23 of white tissue-culture treated 384-well plates containing 0.25 μL of test compound dissolved in 100% DMSO. Fifty microliters of Media II is added to wells in column 24. The plates are incubated at 37° C. (5% $CO_2$) for 24 hours, then 5 μL of Alamar Blue reagent (Trek Diagnostics, Cat #00-100) is added to each well. Plates are then incubated an additional two hours at 37° C., 5% $CO_2$ and then one hour at room temperature. Fluorescence is read at Ex525/Em598. After the fluorescence is measured, 25 μL of luciferase substrate (Steady-Glo, Promega) is added to each well. The plates are incubated for fifteen minutes at room temperature, after which the luminescence is read on a PheraStar (BMG Labtech) plate reader.

Rifampicin (10 μM), a well-known agonist of PXR, is included in each plate as an internal standard and positive control. The data is then expressed as percent control (% CTRL), where the control signal is the signal from the 10 μM rifampicin and the blank signal is that from the DMSO vehicle.

% CTRL=((Compound signal−Blank signal)/(Control signal−Blank signal))*100

Compounds are tested at ten concentrations (2.5 nM-50 μM, 1:3 serial dilution). Assay results are reported as $EC_{50}$, the concentration of compound at which 50% of the maximal response is observed, and as YMAXOBS, the maximal response (highest percent CTRL) observed for that compound. The $EC_{50}$ is defined as the concentration corresponding to half of the maximal response derived from the fitted 20-point curve as determined using a four-parameter logistic regression model. Additionally, compounds may also be reported as $EC_{20}$ or $EC_{60}$.

Data Analysis for HepG2 Cytotoxicity Assay

Compounds are tested at ten concentrations (2.5 nM-50 μM, 1:3 serial dilution). Assay results are reported as $IC_{50}$, defined as the concentration corresponding to 50 percent inhibition as derived from the fitted 20-point curve determined using a four-parameter logistic regression model.

In Vitro Metabolism Assays

Assay Conditions A:
Test compound is received as a 3.5 mM stock solution in 100 percent DMSO. Compound is diluted to create a 50 μM acetonitrile (ACN) solution containing 1.4% DMSO, which is then used as a 100× stock for incubation with microsomes. Each compound is tested in duplicate separately in each of three species in the Metabolic Stability-Human, Rat, and Mouse assay suite or as individual species in the Metabolic Stability-Dog or Metabolic Stability-Monkey suites. Compound, NADPH and liver microsome solutions are combined for incubation in three steps:

152 μL of liver microsome suspension, protein concentration of 1.1 mg/mL in 100 mM $NaP_i$, pH 7.4, 6.6 mM $MgCl_2$ buffer, is pre-warmed at 37° C.

1) 1.7 μL of 50 μM compound (98.6% ACN, 1.4% DMSO) is added to the same tube and pre-incubated at 37° C. for 5 minutes.
2) The reaction is initiated by the addition of 17 μL of pre-warmed 10 mM NADPH solution in 100 mM $NaP_i$, pH 7.4.
3) Reaction components are mixed well, and 75 μL are immediately transferred into 150 μl quench/stop solution (zero-time point, $T_0$). Reactions are incubated at 37° C. for 10 minutes and then an additional 75 μL aliquot is transferred into 150 μL quench solution. Acetonitrile containing 100 μM DMN (a UV standard for injection quality control), is used as the quench solution to terminate metabolic reactions.
4) Quenched mixtures are centrifuged at 1500 rpm (~500×g) in an Allegra X-12 centrifuge, SX4750 rotor (Beckman Coulter Inc., Fullerton, Calif.) for fifteen minutes to pellet denatured microsomes. A volume of 90 μL of supernatant extract, containing the mixture of parent compound and its metabolites, is then transferred to a separate 96-well plate for UV-LC/MS-MS analysis to determine the percent of parent compound that is remaining in the mixture.
5)

| Metabolic Stability Assay - Reaction Components | |
|---|---|
| Reaction Components | Final Concentration in the Metabolic Stability Assay |
| Compound (Substrate) | 0.5 μM |
| NaPi Buffer, pH 7.4 | 100 mM |
| DMSO | 0.014% |
| Acetonitrile | 0.986% |
| Microsomes (human, rat, mouse) (BD/Gentest) | 1 mg/mL protein |
| NADPH | 1.0 mM |
| $MgCl_2$ | 6.66 mM |
| 37° C. Incubation time | 0 minutes and 10 minutes |
| Quench/Stop Solution (ACN + 100 μM DMN) | 150 μL |
| Sample of Reaction | 75 μL |
| Sedimentation of Denatured Microsomes | 15 minutes |
| UV-LC/MS analysis of supernatant | 0.17 μM |

Assay Conditions B:
Test compound is received as 20 mM in DMSO. Compound is diluted to create a 300 μM acetonitrile (ACN) solution containing 1.5% DMSO, which is then used as a 100× stock for incubation with microsomes. Each compound is tested in duplicate separately in each of three species in the Metabolic Stability-Human, Rat, Mouse assay suite or individual species in the Metabolic Stability-Dog or Metabolic Stability-Monkey suites. Compound, NADPH and liver microsome solutions are combined for incubation in three steps:

1. 450 μL of liver microsome suspension, protein concentration of 1 mg/mL in 100 mM $NaP_i$, pH. 7.4, 6.6 mM $MgCl_2$ buffer, are pre-warmed at 37° C.
2. 5 μl of 300 μM compound (98.5% CAN, 1.5% DMSO) is added to the same tube.

3. The reaction is initiated by the addition of 50 μl of pre-warmed 5 mM NADPH solution in 100 mM NaP$_i$, pH 7.4.

Reaction components are mixed well and 150 μL removed to quench/stop solution immediately for the zero-minute time point. Reactions are incubated at 37° C. for 10 minutes and then an additional 150 μL removed from incubation. Aliquots removed are combined with 300 μL ACN which contains 100 μM DMN as a UV standard for detection.

| Reaction Components | Final Concentration in the Metabolic Stability Assay |
|---|---|
| Compound (Substrate) | 3 μM |
| NaPi Buffer, pH 7.4 | 100 mM |
| DMSO | 0.015% |
| ACN | 0.985% |
| Microsomes (human, rat, mouse) (BD/Gentest) | 1 mg/ml protein |
| NADPH | 0.5 mM |
| MgCl$_2$ | 6.66 mM |
| 37° C. Incubation time | 0 minutes and 10 minutes |
| Quench/Stop Solution (ACN + 100 μM DMN) | 300 μL |
| Sample of Reaction | 150 μL |
| Sedimentation of Denatured Microsomes | 15 minutes |
| UV-LC/MS analysis of supernatant- | 1.0 μM |

Quenched mixtures are centrifuged at 1500 rpm (~500×g) in an Allegra X-12 centrifuge, SX4750 rotor (Beckman Coulter Inc., Fullerton, Calif.) for fifteen minutes to pellet denatured microsomes. A volume of 110 μl of supernatant extract, containing the mixture of parent compound and its metabolites, is then transferred to a separate 96-well plate for UV-LC/MS-MS analysis to determine the percent of parent compound that is remaining in the mixture.

As shown below in Table 2, Compound I can also be positively differentiated through 2 critical parameters, PXR transactivation and human liver microsome stability.

PXR transactivation predicts potential drug-drug interactions. If a compound activates this receptor, other drugs may be metabolized quicker than normal leading to lower drug levels and reduced efficacy. This is clearly an unwanted characteristic in a compound that is being considered for development.

The in vitro screen indicates that Compound I is not a significant activator of this receptor relative to all but one of the compounds listed.

Finally, the compounds were tested in the human liver microsome stability assay which is a good predictor of in vivo clearance of a compound. For development purposes, compounds with less than 70% were dropped from further consideration.

Thus, the combination of the low risk of PXR transactivation along with the 100% of compound remaining in the human liver microsome metabolism assay shows that Compound I has superior pharmacological characteristics when compared with other known and structurally similar CCR-1 antagonists.

TABLE 2

PXR/Cyp 3A4 Induction potential and Metabolic Stability - In Vitro:

| Example #* | CCR1 K$_i$ (nM) | PXR EC$_{50}$ (μM) | Human Liver Microsomal Metabolism % remaining (Assay Conditions) |
|---|---|---|---|
| Compound I | 0.7 | >25 | 100% (B) |
| #1356 | 3.7 | 1.83 | 100% (A)/100% (B) |

TABLE 2-continued

PXR/Cyp 3A4 Induction potential and Metabolic Stability - In Vitro:

| Example #* | CCR1 K$_i$ (nM) | PXR EC$_{50}$ (μM) | Human Liver Microsomal Metabolism % remaining (Assay Conditions) |
|---|---|---|---|
| #1083 | 2.6 | 1.9 (EC$_{20}$) | 13% (A) |
| #460 | 0.7 | 0.53 | 47% (A)/16% (B) |
| #466 | 2.6 | 1.12 (EC$_{60}$) | 67% (A)/33% (B) |
| #850 | 0.5 | 10.2 (EC$_{60}$) | 99% (A) |
| #897 | 2.1 | >50 (EC$_{60}$) | 59% (A) |

(*)- Examples from US2007/0208056 as shown below:

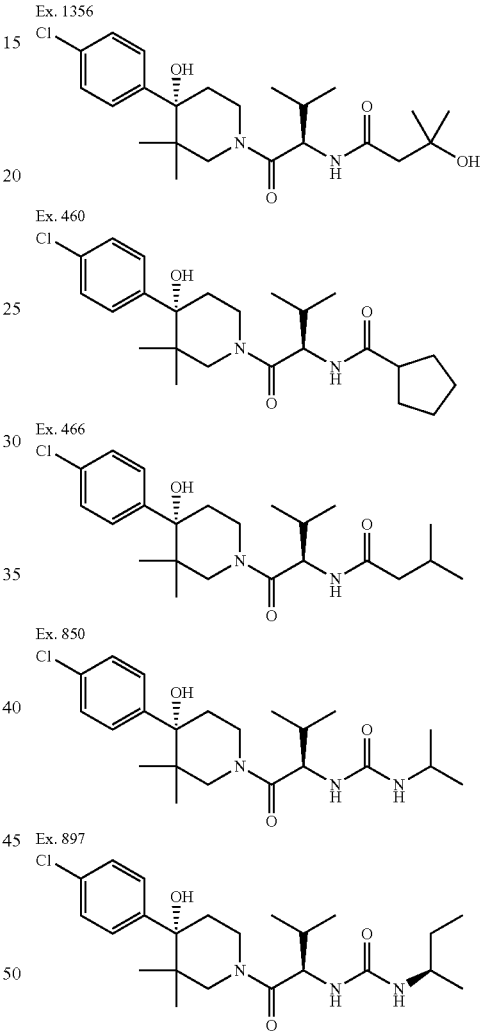

Ex. 1356

Ex. 460

Ex. 466

Ex. 850

Ex. 897

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to a compound of formula (I) which is believed to be useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and arthrosclerosis.

For example, the instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, the instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for the instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated.

However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, arthrosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (*Trichuriasis, Enterobiasis, Ascariasis, Hookworm, Strongyloidiasis, Trichinosis, filariasis*); trematodes (flukes) (*Schistosomiasis, Clonorchiasis*), cestodes (tape worms) (*Echinococcosis, Taeniasis saginata, Cysticercosis*); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of the compound of formula (I) in the preparation and execution of screening assays for compounds that modulate the activity of chemokine receptors. Furthermore, the compound of this invention is useful in establishing or determining the binding site of other compounds to chemokine receptors, e.g., by competitive inhibition or as a reference in an assay to compare its known activity to a compound with an unknown activity. When developing new assays or protocols, the compound according to the present invention could be used to test their effectiveness. Specifically, such compound may be provided in a commercial kit, for example, for use in pharmaceutical research involving the aforementioned diseases. The compound of the instant invention is also useful for the evaluation of putative specific modulators of the chemokine receptors. In addition, one could utilize the compound of this invention to examine the specificity of G protein coupled receptors that are not thought to be chemokine receptors, either by serving as examples of compounds which do not bind or as structural variants of compounds active on these receptors which may help define specific sites of interaction.

The compound of formula (I) is used to treat or prevent disorders selected from rheumatoid arthritis, osteoarthritis, septic shock, arthrosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, glomerulonephritis, and systemic lupus erythematosus.

In another aspect, the compound of formula (I) is used to treat or prevent inflammatory disorders selected from rheumatoid arthritis, osteoarthritis, arthrosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compound is used to treat or prevent inflammatory disorders selected from rheumatoid arthritis, osteoarthritis, arthrosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and arthrosclerosis, and those pathologies noted above is illustrated by the combination of the compound of this invention and other compounds which are known for such utilities. For example, in the treatment or prevention of inflammation, the present compound may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, the compound of formula (I) may be used in combination with other drugs that are used in the treatment/prevention/suppression or amelioration of the diseases or conditions for which the compound of the present invention is useful. Such other drugs may be administered, by a route and in an amount commonly used therefore, contemporaneously or sequentially with a compound of the present invention. When the compound of formula (I) is used contemporaneously with one or more other drugs, a pharmaceutical composition containing such other drugs in addition to the compound of formula (I) may be used. Accordingly, the pharmaceutical compositions of the present invention include those that also contain one or more other active ingredients, in addition to the compound of formula (I).

Examples of other active ingredients that may be combined with the compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvastatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone and pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (n) other compound such as 5-aminosalicylic acid and prodrugs thereof, anti-metabolites such as azathioprine and 6-mercaptopurine, and cytotoxic cancer chemotherapeutic agents. The weight ratio of the compound of formula (I) to the second active ingredient may be varied and will depend upon the effective doses of each ingredient.

Generally, an effective dose of each will be used. Thus, for example, when the compound of formula (I) is combined with an NSAID the weight ratio of the compound of the present invention to the NSAID will generally range from about 1000:1 to about 1:1000, or alternatively from about 200:1 to about 1:200. Combinations of the compound of formula (I) and other active ingredients will generally also be within the aforementioned range, but in each case, an effective dose of each active ingredient should be used.

The compound is administered to a mammal in a therapeutically effective amount. By "therapeutically effective amount" it is meant an amount of the compound of Formula I that, when administered alone or in combination with an additional therapeutic agent to a mammal, is effective to prevent or ameliorate the thromboembolic disease condition or the progression of the disease.

Dosage and Formulation

The compound of this invention can be administered in such oral dosage forms as tablets, capsules (each of which includes sustained release or timed release formulations), pills, powders, granules, elixirs, tinctures, suspensions, syrups, and emulsions. It may also be administered in intravenous (bolus or infusion), intraperitoneal, subcutaneous, or intramuscular form, all using dosage forms well known to those of ordinary skill in the pharmaceutical arts. It can be administered alone, but generally will be administered with a pharmaceutical carrier selected on the basis of the chosen route of administration and standard pharmaceutical practice.

The dosage regimen for the compound of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion.

The compound of this invention may be administered in a single daily dose, or the total daily dosage may be administered in divided doses of two, three, or four times daily.

The compound of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compound is typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compound of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compound of this invention is combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compound of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:

1. A method for preparing a medicament for the treatment of inflammation comprising formulating the compound of Formula (I):

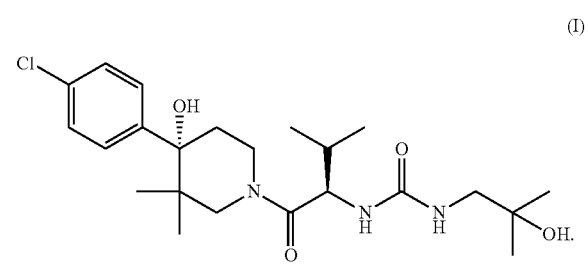

2. A method for preparing a medicament for the treatment of inflammation comprising formulating a composition of a compound of Formula (I):

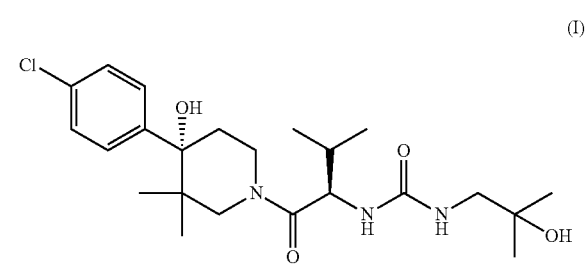 [SMILES: CC(C)[C@@H](NC(=O)NCC(C)(C)O)C(=O)N1CC[C@](O)(c2ccc(Cl)cc2)C(C)(C)C1]

into a useful pharmaceutical dosage form.

3. The method of claim 1 or 2, wherein the inflammation is associated with rheumatoid arthritis.

4. The method of claim 1 or 2, wherein inflammation is associated with fibrotic disease.

5. The method of claim 1 or 2, wherein the inflammation is associated with renal fibrosis.

6. The method of claim 1 or 2, wherein the inflammation is associated with cystic fibrosis.

7. The method of claim 1 or 2, wherein the inflammation is associated with interstitial lung diseases (ILD).

8. The method of claim 6, wherein the interstitial lung disease is idiopathic pulmonary fibrosis.

* * * * *

UNITED STATES PATENT AND TRADEMARK OFFICE
CERTIFICATE OF CORRECTION

PATENT NO. : 8,633,226 B2  Page 1 of 1
APPLICATION NO. : 13/628180
DATED : January 21, 2014
INVENTOR(S) : Joseph B. Santella It is certified that error appears in the above-identified patent and that said Letters Patent is hereby corrected as shown below:

On the Title Page:

Item (56) References Cited, under FOREIGN PATENT DOCUMENTS:
    Column 2, change "WO 02/092682" to -- WO 02/092582 --.

Item (56) References Cited, under OTHER PUBLICATIONS:
    Page 2, Column 2, F.Z. Dorwald reference, line 3, change "Wienheim" to -- Weinheim --.

Signed and Sealed this
Twenty-fourth Day of March, 2015

Michelle K. Lee
*Director of the United States Patent and Trademark Office*